United States Patent [19]

Rabinowitz

[11] Patent Number: 5,175,901
[45] Date of Patent: Jan. 5, 1993

[54] APPARATUS AND METHOD FOR BRUSHING TEETH

[76] Inventor: Gary A. Rabinowitz, 134 W. 58th St., #505, New York, N.Y. 10019

[21] Appl. No.: 694,357

[22] Filed: May 1, 1991

[51] Int. Cl.⁵ .......................... A46B 1/00; A46B 9/02
[52] U.S. Cl. .................................. 15/167.2; 15/167.1; 15/22.1; 15/22.2; 128/62 A
[58] Field of Search .................... 15/22.1, 167.2, 22.2; 128/859–862, 62 A

[56] References Cited

U.S. PATENT DOCUMENTS

| | | | |
|---|---|---|---|
| 803,475 | 10/1905 | Dennis | 128/62 A |
| 2,257,709 | 9/1941 | Anderson | 15/167.2 |
| 3,527,218 | 9/1970 | Westine | 128/62 A |

Primary Examiner—Philip R. Coe
Assistant Examiner—Patrick Brinson
Attorney, Agent, or Firm—Davis, Hoxie, Faithful & Hapgood

[57] ABSTRACT

An apparatus for brushing an entire arch of teeth at once has a resilient U-shaped housing containing a channel within which the arch of teeth fits. A plurality of bristles substantially covers the surface area of the channel, and a handle extends from each arm of the housing. The channel is shaped whereby the bristles on the edges of the channel are angled into the gingival sulcus. In operation, the user grasps a handle in each hand and moves the handles in opposition to each other to move the resilient housing. This causes the bristles to move, thereby brushing the teeth in an effective manner.

7 Claims, 6 Drawing Sheets

APPARATUS AND METHOD FOR BRUSHING TEETH

FIELD OF THE INVENTION

This invention relates to tooth brushing and cleaning apparatuses and methods, and particularly to a brush that fits in the mouth and brushes an entire row of teeth simultaneously.

BACKGROUND OF THE INVENTION

The dental profession recommends certain general guidelines for brushing teeth with a conventional toothbrush. Teeth should be brushed in the morning, at night before retiring, and after meals. At least once during the day, the brushing should be performed continuously for ten minutes. During brushing, the biting surfaces and side surfaces of the teeth should be scrubbed, and the gingival sulcus, a narrow crevice beneath the gumline between the gingiva (gums) and the teeth, should be cleaned by aiming the bristles of the toothbrush at the gumline at a 45 degree angle from vertical. Preferably, the toothbrush is moved in a small circular motion to clean the gingival sulcus. Through this motion, the bristles work into the gingival sulcus and lift debris out of it. Pressure of the toothbrush against the area being cleaned should be gentle where cleaning the gingival sulcus and massaging the gums; the pressure may be somewhat greater where scrubbing the biting surfaces of the teeth.

These guidelines, although effective, are rarely followed. Most people do not brush nearly long enough; a typical person brushes his teeth for approximately one minute per day, which results in less than two seconds of brushing per tooth surface. This is inadequate for good oral hygiene. Additionally, most people do not implement the intricate brushing motion recommended by the above guidelines, which motion necessarily requires a high level of concentration and manual dexterity. Elderly, arthritic, or otherwise impaired persons may not be able physically to brush their teeth in the recommended manner.

A number of different types of brushes have been developed in an attempt to overcome these disadvantages. Many of these fit over and brush an entire arch of teeth at one time (there are two arches, or rows, of teeth in the mouth: an upper and a lower). Brushing an entire arch at once reduces the time required to brush all the exposed surfaces of the teeth. In many of these apparatuses, brushing is carried out by chewing motion while the brush is in the mouth. Examples of such apparatuses include U.S. Pat. No. 3,769,652 to Rainer, U.S. Pat. No. 4,237,574 to Kelly et al., and U.S. Pat. No. 3,874,084 to Cole. The chewing motion, however, is non-uniform, and there is no assurance that the bristles of the brush will move in the recommended way. Additionally, since the brushing device in all of these patents fits completely over the teeth (i.e., all the way down the sides thereof), the bristles projecting from the sides of the device that are used to brush the side surfaces of the teeth tend to stick straight out from the device and are therefore oriented perpendicular to the gumline instead of at the recommended 45 degrees.

A tooth brushing device disclosed in U.S. Pat. No. 4,011,616 to Kennedy addresses the problem of proper movement by carrying out brushing motion through a single connection to a vibratory device at the front of the arch. However, proper functioning requires that a rigid skeletal structure be placed along the length of the arch, which adds to the bulk of the device and increases user discomfort. A patent to Solow, U.S. Pat. No. 4,224,710, discloses a tooth brushing device that mechanically moves individual groups of bristles around each tooth. This apparatus, however, is bulky, and cleans the gingival sulcus with vertical motion only instead of the recommended circular motion.

There remains a need for a small convenient tooth brushing apparatus that can brush an entire arch of teeth at once, while carrying out the recommended tooth brushing motion.

OBJECTS AND SUMMARY OF THE INVENTION

It is therefore an object of the present invention to provide a tooth brushing device that overcomes the shortcomings of the prior art.

It is a further object of the invention to provide a tooth brushing device that is able to clean an entire arch of teeth at one time without being unduly bulky or cumbersome.

It is a further object of the invention to provide a tooth brushing device and method that carries out the recommended motion and pressure for brushing teeth without need for great manual dexterity.

It is a further object of the invention to provide a tooth brushing device that positions the bristles at the correct angle to the gumline.

In accordance with a principal aspect of the invention, an apparatus for brushing teeth comprises an arcuate housing, defined by a first arm, a central portion, and a second arm. A channel is disposed along the length of the housing for placement over an arch of teeth. A handle extends from the first arm of the housing.

In accordance with a second aspect of the invention, an apparatus for brushing teeth comprises an arcuate resilient housing defined by a first arm, a central portion, and a second arm. A channel adapted for placement over an arch of teeth is disposed along the length of the housing, said channel being defined by a first wall, a base portion, and a second wall. The walls and base portion of the channel define a trough, the base portion becoming increasingly narrow from the back to the front of the arch. Preferably, bristles for brushing the teeth are disposed generally normal to the surface of the channel, whereby when the channel is placed over the arch of teeth to be brushed, the bristles on the walls of the channel are angled approximately 45 degrees from vertical, and whereby the bristles at the base portion of the channel are approximately vertical.

In accordance with a third aspect of the invention, a method for brushing an arch of teeth comprises the steps of placing an arcuate housing, having a channel disposed along the length of the housing and a handle on each arm of the housing, over the arch of teeth to be brushed, and moving the handles in opposition to each other, preferably in a circular motion, causing the housing to move along the arch of teeth.

Specifically, and in a principal embodiment, an apparatus for brushing an entire arch of teeth at one time comprises a U-shaped resilient housing, defined by a first arm, a central portion, and a second arm, which approximates the shape of the arch of teeth to be brushed. A channel formed in a first side of the housing for placement over the arch of teeth is defined by a first wall, a base portion, and a second wall. The walls and base portion define a trough, which is relatively shallow over the teeth at the rear of the arch, becoming progressively steeper as it approaches the teeth at the front of the arch. The base portion likewise progressively narrows. Bristles are mounted to the channel and substantially cover the surface of the channel. A first and second handle extend from the first and second arms of the housing, respectively.

BRIEF DESCRIPTION OF THE DRAWINGS

These and other objects, aspects, and embodiments of the present invention will be described with reference to the following drawing figures, of which.

DETAILED DESCRIPTION OF THE DRAWINGS

Figure 1:
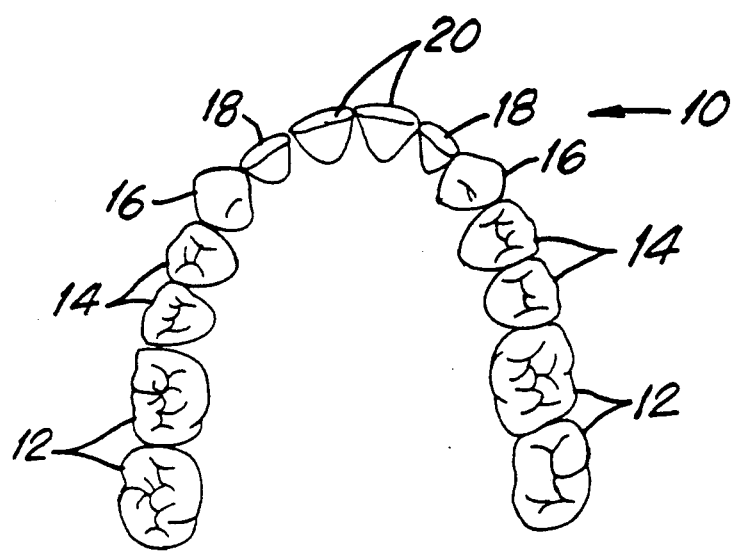
FIG. 1 is a top plan view of an arch of a typical upper row of teeth.
Figure 2:
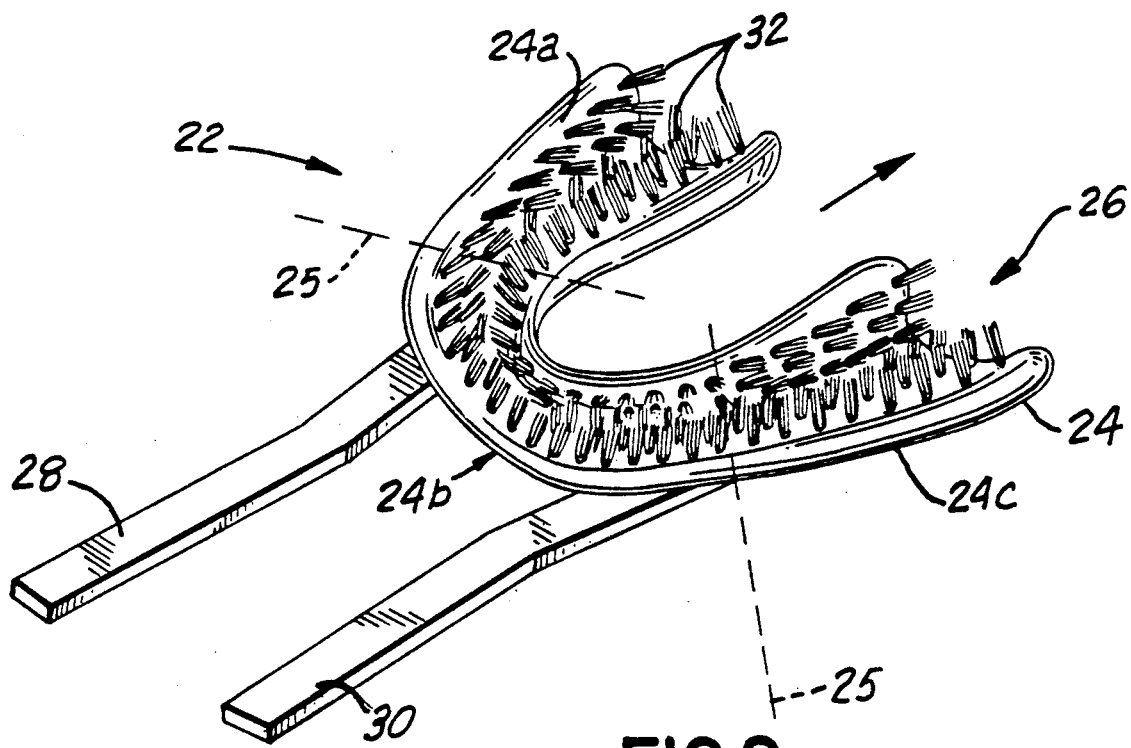
FIG. 2 is a perspective view of a preferred embodiment of a tooth brushing apparatus of the present invention.

Referring first to FIG. 1, a brief description of a typical arch of human teeth will assist in an understanding of the present invention. FIG. 1 depicts an arch 10 of the upper row of teeth. The arch of the lower row of teeth is similar in all relevant respects, including the general arcuate shape of the arch. Four molars 12 are located on the free ends of the arch 10, and thus at the back of the mouth, with two on each end. Four premolars 14 are located immediately in front of the molars 12. The molars 12 and the premolars 14 have flat and broad top surfaces, with the top surface area of the premolars 14 being slightly less than that of the molars 12. These broad top surfaces render the molars 12 and premolars 14 suitable for mashing motion. The molars 12 and premolars 14 have well-defined sides and tops, and are generally rectangular in cross-section. Two canine teeth 16 are located in front of the premolars 14.

The canine teeth 16 are pointed, which makes them suitable for tearing motion, and are thick at their base, while rising to a point at their tips. The canine teeth 16 therefore have little top surface area, and have sides that are sloped. Two lateral incisors 18 and two front incisors 20 are located at the front of the arch 10. The incisors 18 and 20 have sharp edges for biting and cutting. The bases of the incisors 18 and 20 are narrower than those of the canine teeth 16, so, although like the canine teeth 16 they have little top surface area, their sides are steeper than those of the canine teeth 16.

Referring now to FIGS. 2-4 and 6-8, a preferred embodiment of a tooth brushing apparatus 22 according to the present invention comprises a U-shaped resilient housing 24. The housing 24 is defined by a first arm 24a, a central portion 24b, and a second arm 24c. Lines 25 in FIGS. 2 and 3 serve as the approximate boundaries between the arms 24a and 24c and central portion 24b. The housing 24 is manufactured from suitably resilient elastomeric material that is inert to saliva, such as polyethylene or silicone rubber, and is curved to form a channel 26 on one side. The channel 26 fits over the arch of teeth to be brushed.

Figure 5:
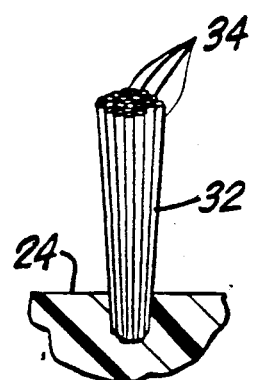
FIG. 5 is a perspective view of an example of a bristle used in the apparatus of FIG. 2.

The channel 26 is substantially uniformly covered with bristles 32. The bristles 32 are anchored in the resilient housing 24 by heat molding, adhesive, or other attachment means known in the art. As shown in FIG. 5, each bristle 32 comprises in the preferred embodiment a group of polished rounded-end nylon fibers 34. This type of bristle is the most efficient in cleaning the teeth, and is the least damaging and traumatic to the gingiva and gingival sulcus. In the preferred embodiment, the channel 26 and bristles 32 are arranged such that the ends of the bristles define a shape closely approximating the shape of the teeth, but slightly smaller, whereby the channel 26 flexes slightly when placed over the teeth. The bristles 32 therefore fit snugly over the teeth and impart a gentle pressure thereto.

Figure 3:
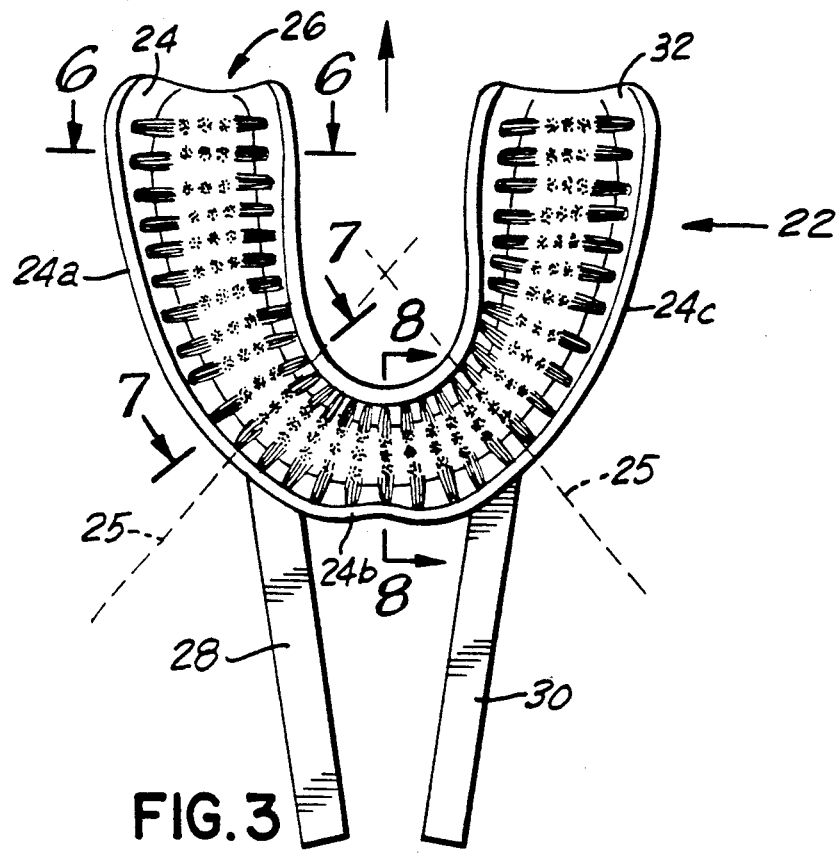
FIG. 3 is a top plan view of the brushing apparatus of FIG. 2.
Figure 4:
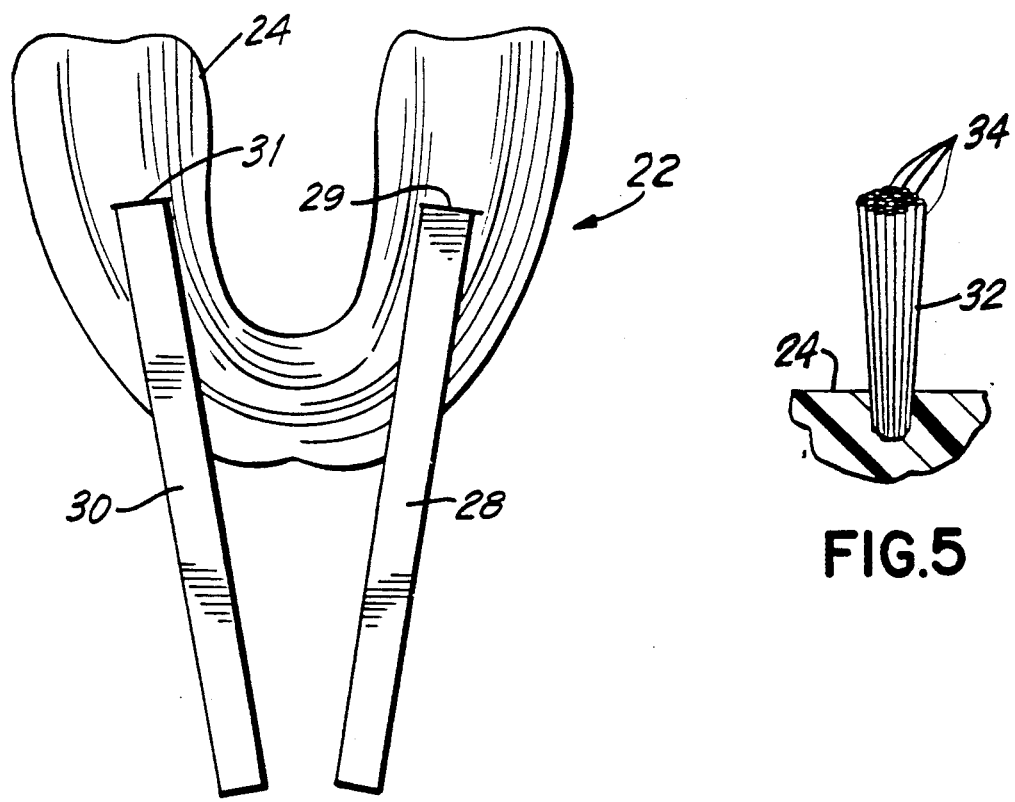
FIG. 4 is a bottom plan view of the brushing apparatus of FIG. 2.

A right handle 28 and a left handle 30 (from the perspective of the user) are attached by adhesive or other suitable means to the surface of the housing 24 at points 29 and 31, respectively (FIG. 3). In the preferred embodiment, the handles 28 and 30 are rectilinear, bent slightly to ease manipulation, and made of hard plastic or other suitable rigid material, although they may be made of the same material as the housing 24 and be integral therewith, if desired. The shape of the handles 28 and 30 may be varied in the same manner as the handle of a conventional toothbrush. The attachment points 29 and 31 of the handles 28 and 30 are on the arms 24a and 24c, respectively, of the U-shaped housing 24, directly beneath the channel 26. The attachment points 29 and 31 are in the area of the premolars 14 when the apparatus 22 is placed over the arch of teeth 10 to be brushed.

The location of the attachment points 29 and 31 of the handles 28 and 30 may be varied, if desired. Thus, they may be located nearer the front of the mouth, in the area of the canine teeth 16 or lateral incisors 18, or nearer the rear of the mouth, in the area of the molars 12. Likewise, their location on the bottom of the housing 24, directly beneath the channel 26 and thus opposite the top surfaces of the teeth, may be changed to either side of the housing 24, opposite the sides of the teeth. The angle at which the handles leave the housing may also be varied.

Since the handles 28 and 30 attach only at the two points 29 and 31 along the arch, the material from which the housing 24 is made and the thickness thereof may be varied throughout the housing 24 to allow the apparatus 22 to move evenly over the arch of teeth without bending or kinking. In the preferred embodiment, the housing 24 is thicker, and therefore stiffer and stronger, in the area immediately around the points 29 and 31, since stress is greater in those areas than in other areas during operation of the apparatus 22. Alternatively, selected parts of the housing 24 may be constructed of rigid materials in conjunction with the main resilient material in order to avoid kinking and/or to ease operation of the apparatus 22.

Figure 6:
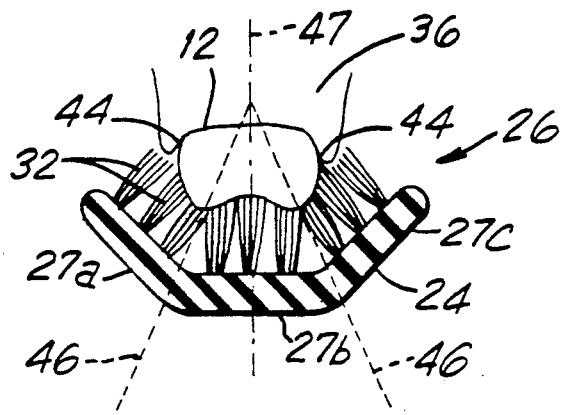
FIG. 6 is a cross sectional view along line 6—6 in FIG. 3.
Figure 7:
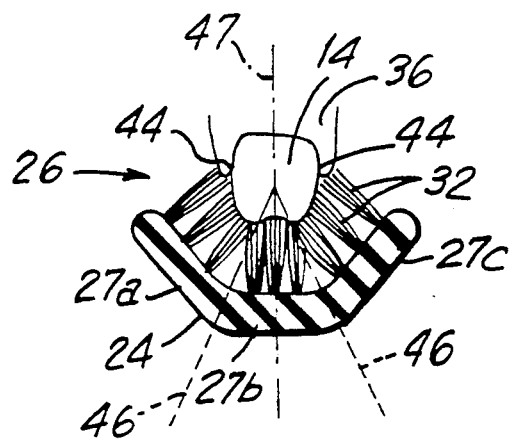
FIG. 7 is a cross sectional view along line 7—7 in FIG. 3.
Figure 8:
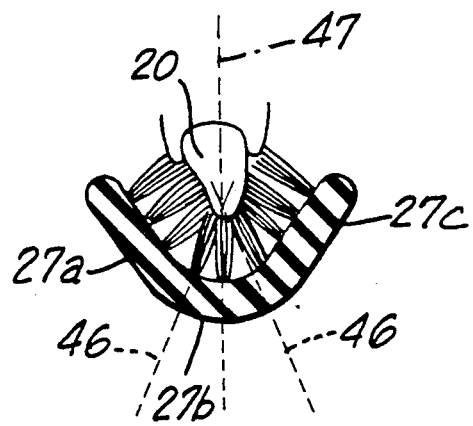
FIG. 8 is a cross sectional view along line 8—8 in FIG. 3.

Referring now to FIGS. 6–8, the channel 26 is defined by a first wall at 27a, a base portion at 27b, and a second wall at 27c, which jointly form a trough. Dotted lines 46 serve as the approximate boundaries of the first wall 26a, base portion 26b and second wall 26c.

In the preferred embodiment of the invention, the walls 27a and 27c of the channel 26 do not come all the way around the sides of the teeth and gums. (If that were the case, the walls 27a and 27c would form a right angle with the base portion 27b and be oriented vertically, i.e., parallel to the vertical dashed line 47.) Rather, the walls 27a and 27c are only slightly angled from the base portion 27b, a configuration which makes the apparatus 22 less bulky. It also aids in cheaper manufacture, since the bristles 32 can be oriented at the angle recommended for brushing simply by mounting them normal (perpendicular) to the surface of the channel 26. All the bristles 32 are therefore mounted at the same angle relative to their point of attachment to the housing 24.

Preferably, the base portion 27b is made stiffer than the walls 27a and 27c, either by thickening the housing or using more rigid materials. This aids in flexion of the housing when it is placed over the teeth, as described above. It also varies the pressure of the apparatus 22 on the surfaces to be cleaned, imparting a firm pressure to the biting surfaces of the teeth and a gentler pressure on the gingiva.

FIG. 6 depicts a cross-section of the apparatus 22 along line 6—6 of FIG. 3, in the area of a molar 12 of the arch 10. The bristles 32 mounted to the first wall 27a of the channel 26 are oriented approximately 45 degrees from vertical, as shown by their angle from the vertical dashed line 47. This orientation enables the bristles 32 mounted to the first wall 27a to enter the gingival sulcus 44 and remove debris from it. Although a 45 degree angle, approximately, is most efficient in reaching into the gingival sulcus 44, the bristles 32 may of course be oriented at other angles. The bristles 32 mounted to the first wall 27a also scrub the inner surface of the molar 12 and massage the inner surface of the gingiva 36.

The bristles 32 mounted to the base portion 27b of the channel 26, which brush the top of the teeth, are oriented approximately straight onto the top of the molar 12 for the most efficient brushing. There is no need to angle the bristles 32 mounted to the base portion 27b, since their purpose is merely to scrub the top of the molar 12, and not to remove debris from the gingival sulcus 44.

The bristles 32 attached to the second wall 27c of the channel 26 are, like the bristles mounted to the first wall 27a, oriented approximately 45 degrees from vertical, as shown by their angle from the vertical dotted line 47. This orientation allows the bristles mounted to the second wall 27c to enter and remove debris from the gingival sulcus 44, and also to brush and massage the outer surface of the molar 12 and surrounding gingiva 36.

FIG. 7 depicts a cross-section of the apparatus 22 along line 7—7 of FIG. 3 in the area of a pre-molar tooth 14. The base portion 27b of the channel 26 is smaller in FIG. 7 than in FIG. 6, since there is less top surface area to be brushed on the premolar 14 than on the molar 12. In the preferred embodiment, as shown, the narrowness of the pre-molar 14 is also compensated for by slightly increasing the angle of the walls 27a and 27c relative to the base portion 27b. If desired, however, the apparatus 22 can adapt to narrower teeth solely by narrowing the base portion 27b or by lengthening the bristles 32.

In FIG. 7, the bristles 32 mounted to the first wall 27a of the channel 26, oriented at approximately 45 degrees from vertical as shown by their angle relative to the vertical dashed line 47, enter the gingival sulcus 44, remove debris from it, and brush and massage the inner surface of the pre-molar 14 and surrounding gingiva 36. The bristles 32 mounted to the base portion 27b scrub the top of the pre-molar 14. The bristles 32 mounted to the second wall 27c, which are oriented at approximately 45 degrees relative to vertical as shown by their angle relative to the vertical dashed line 47, remove debris from the gingival sulcus 44 and brush and massage the outer surface of the pre-molar 14 and surrounding gingiva 36.

FIG. 8 depicts a cross-section of the apparatus 22 along line 8—8 of FIG. 3 in the area of a front incisor 20. The base portion 27b is smaller in FIG. 8 than in FIG. 7, since the incisor 20 is narrower than the canine tooth 16. The narrowness of the front incisor is also compensated for by slightly increasing the angle of the walls 27a and 27c relative to the base portion 27b. The bristles 32 mounted to the first wall 27a, base portion 27b, and second wall 27c are oriented around the incisor 20 in a similar fashion to the bristles 32 around the canine tooth 16 and the molar 12, except that there are fewer bristles mounted to the base portion 27b.

It will be appreciated that the 45 degree angle of the bristles 32 mounted to the first and second walls 27a and 27c relative to vertical is approximate. It will also be appreciated that the bristles 32 comprise a continuum of angles corresponding to the curvature of the channel 26, whereby the angles of the bristles mounted to each of the walls 27a and 27c and base portion 27b need not be sharply defined, but can gradually change as they approach the adjacent areas.

The housing 24 may be made in varying sizes to accommodate different arch sizes. These stock sizes will fit the arches of most persons. Many oddly shaped arches will also fit into a stock size, since the housing 24 is resilient, whereby it can conform to different shapes to a limited extent. The apparatus 22 may be custom made for those persons having a very unusual arch form. In any case, the housing should be designed to minimize interference with other structures of the mouth such as the tongue, cheeks, and roof of the mouth, and to minimize bulk, too much of which tends to make the user gag.

The channel 26 is shaped such that the length of the bristles 32 is close to that of a conventional toothbrush. This length provides resiliency in the bristles 32, which, in conjunction with the resiliency of the housing 24, enables the apparatus 22 to accept a wider range of arch sizes and shapes, and which increases comfort and imparts the proper pressure during use. If desired, the bristles 32 attached to the base portion 27b of the channel 26 may be made shorter than the bristles on the walls 27a and 27c in order to reduce bulk.

Conventional toothbrushes vary the pressure put on the teeth and gums during brushing by varying the stiffness of the bristles. To vary the pressure put on the teeth and gums by the apparatus 22, the shape of the channel 26 may be changed to allow for shorter or longer bristles. The pressure can also be varied by changing the resiliency and/or thickness of the housing or the length and/or stiffness of the bristles. Such variation will provide a range of options for customers, who can choose among them according to their individual preferences. Hard and soft bristles can also be used together, such as attaching hard bristles to the base portion 27b and soft bristles to the walls 27a and 27c.

Figure 9:
FIG. 9 is a perspective view of a person using the brushing apparatus of FIG. 1 to brush his teeth.

FIG. 9 depicts the apparatus 22 in the mouth of a user 50. In operation, the apparatus 22 is inserted in the mouth of the user 50, in the direction indicated by the arrows in FIGS. 2 and 3, and the channel 26 is fitted over either the top or bottom arch of teeth. While in use over the arch of upper teeth 10, the user 50 grasps the handle 28 in his right hand and the handle 30 in his left hand, and moves the handles 28 and 30 in opposition to each other, pushing one while pulling the other, to brush his teeth. The movement is reversed repeatedly. The manipulation of the handles 28 and 30 cyclically moves the housing 24 around the arch 10. Preferably, the user 50 moves the handles 28 and 30 up and down slightly as well (in approximately a circular motion), causing the tips of the bristles 32 to accomplish a circular motion. This is the preferred motion for cleaning out the gingival sulcus 44. The amplitude of the motion will depend on the vigor of the user 50 and the degree of resiliency of the housing 24, i.e., how much the housing 24 will deform to allow travel around the arch 10. Simple back and forth motion may be used, if desired.

To brush the lower arch, the user 50 grasps the handle 30 in his right hand and the handle 28 in his left hand, and manipulates them as described above.

For the conventional toothbrush, a large ribbon of toothpaste is placed at the head of the toothbrush and spread around the mouth upon brushing. In the present invention, the most desirable way of dispensing the toothpaste is to spread a thin ribbon of toothpaste, e.g., 1-2 millimeters in diameter, in a zigzag line along the length of the channel 26 of the housing 24. Such a thickness of toothpaste could be achieved by placing an adaptor onto conventional tubes or pumps of toothpaste.

Figure 10:
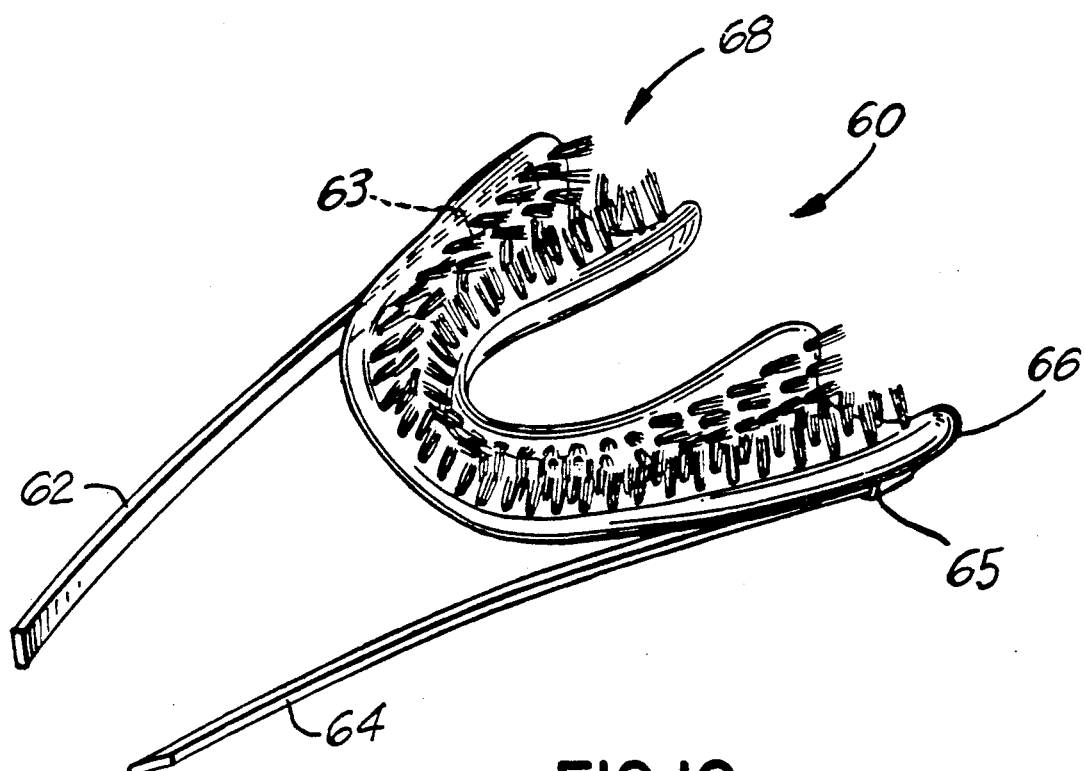
FIG. 10 is a perspective view of a second embodiment of a tooth brushing apparatus of the present invention.

FIG. 10 depicts another embodiment of a tooth brushing apparatus 60 according to the invention, which is identical in all respects to the apparatus 22 in FIGS. 2-9 except in the location of the attachment points 63 and 65 of the handles 62 and 64 to the housing 66. The handles 62 and 64 are placed on the outer side of the housing 66 instead of directly beneath the channel 68. Additionally, the attachment points 63 and 65 are located in the area of the molars 12, farther back from the attachment points 29 and 31 in FIGS. 2-9. The embodiment 60 of FIG. 10, whose handles 62 and 64 are farther apart than the handles 28 and 30 in FIGS. 1-8, may be used to ease manipulation of the handles during Operation of the apparatus 60.

Figure 11:
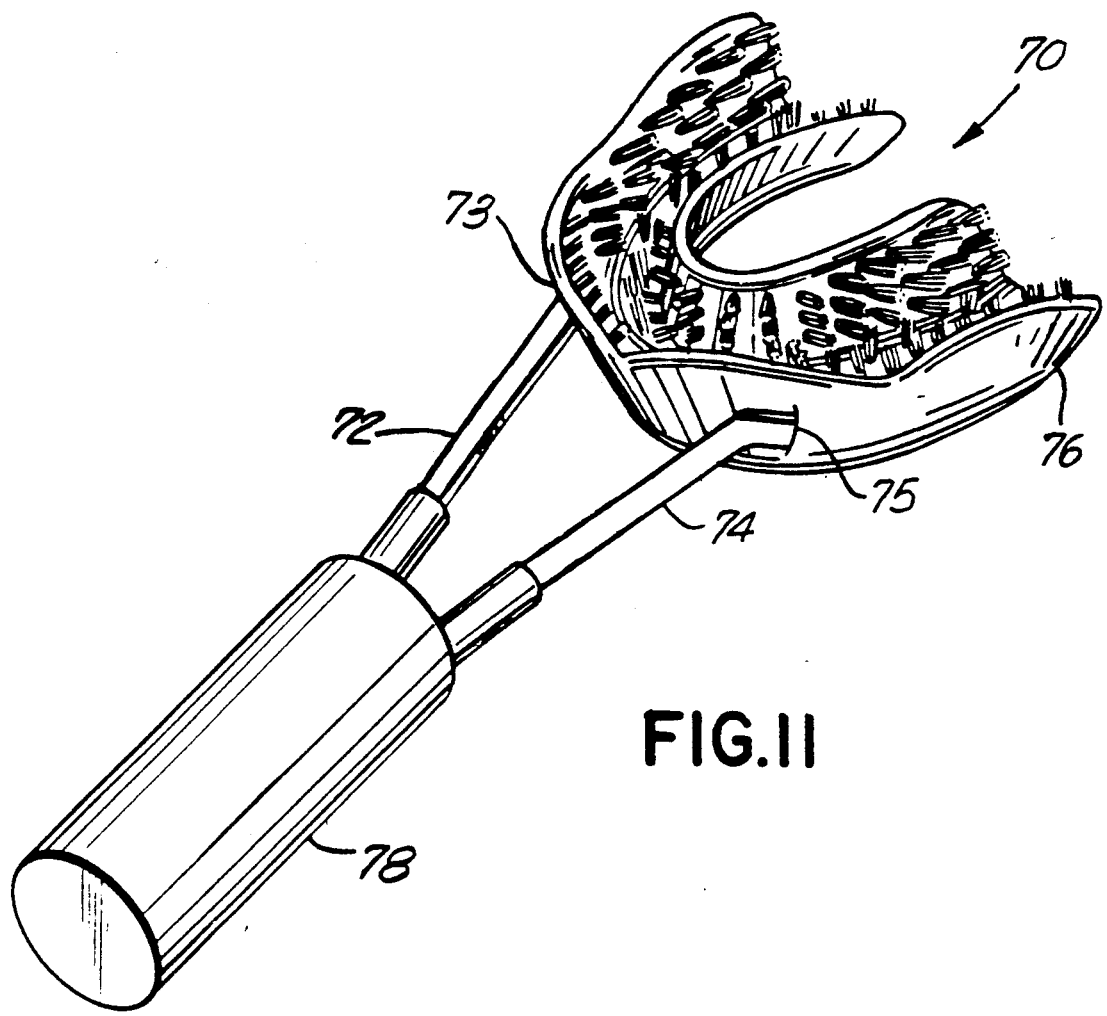
FIG. 11 is a perspective view of a third embodiment of a tooth brushing apparatus of the present invention.

FIG. 11 depicts another embodiment of a tooth brushing apparatus 70 according to the invention. The apparatus 70 is similar to the apparatus 22 of FIGS. 2-9. However, the channel 71 in the apparatus 70 is deeper and more angular than the channel 26 in the apparatus 22. In addition, the handles 72 and 74 are attached to the housing 76 in the area of the canine teeth 16, at attachment points 73 and 75, and are bent to point approximately straight out from the housing 76. (The handles may bent as desired in any embodiment of the invention.) The free ends of the handles 72 and 74 are attached to a vibratory machine 78, which moves the handles 72 and 74 back and forth automatically. The use of this device is advisable for those who are unable to brush their teeth adequately by hand, such as the elderly or infirm. The location of the attachment points 73 and 75 in the area of the canine teeth 16 makes it slightly more difficult to move the housing 76 to brush the teeth, but has the advantage of placing the handles closer together as they leave the mouth, making the apparatus 70 more comfortable in the mouth of the user. A vibratory machine may of course be used with other configurations of the apparatus.

Figure 12:
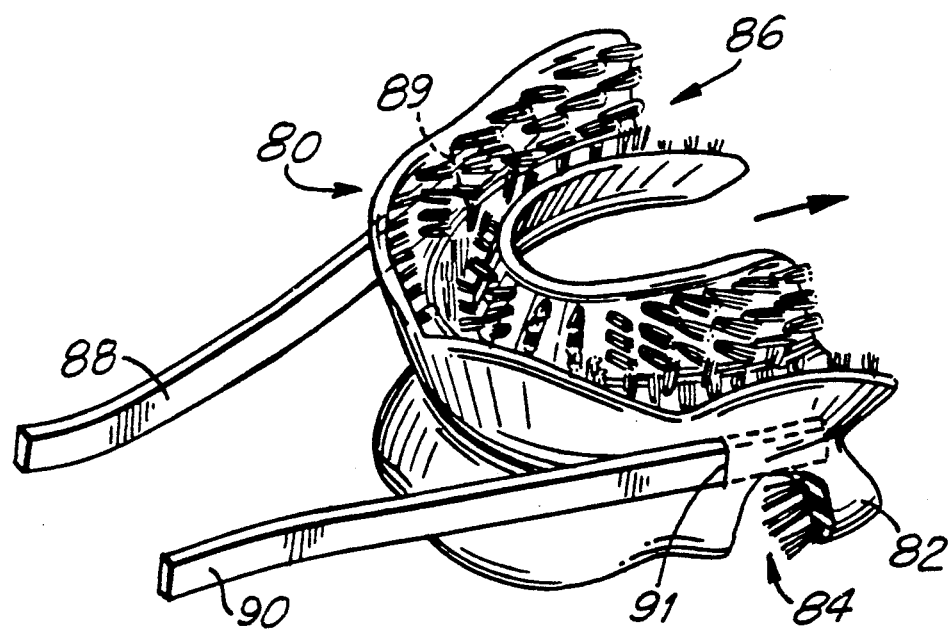
FIG. 12 is a perspective view of a fourth embodiment of a tooth brushing apparatus of the present invention.

FIG. 12 depicts another embodiment of a tooth brushing apparatus 80 according to the invention, in which the two rows of teeth are brushed at the same time. The tooth brushing apparatus 80 comprises a resilient housing 82 containing a lower channel 84 and an upper channel 86, both similar to the channel 71 in FIG. 11. A right handle 88 and a left handle 90 are attached to the right and left sides, respectively, of the housing 82, at the midpoint between the top and the bottom of the housing 82, at attachment points 89 and 91. The attachment points 89 and 91 may be located higher or lower if it is desired to brush one arch of teeth more thoroughly than the other. Except for the two channels 84 and 86 and the location of the attachment points 89 and 91 of the handles 88 and 90 to the housing 82, the tooth brushing apparatus 80 is similar in structure and operation to the apparatus 22 in FIGS. 2-9. The apparatus 80 has the advantage of brushing both arches of teeth at the same time.

Figure 13:
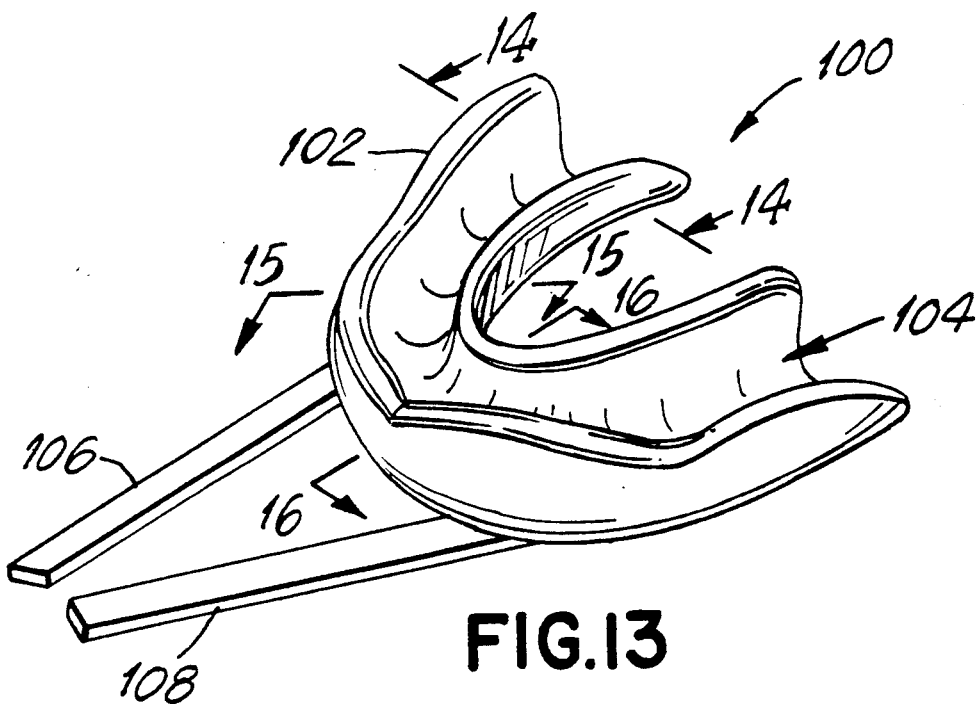
FIG. 13 is a perspective view of a fifth embodiment of a tooth brushing apparatus of the present invention.
Figure 14:
FIG. 14 is a cross sectional view along line 14—14 in FIG. 13.
Figure 15:
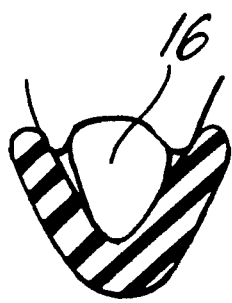
FIG. 15 is a cross sectional view along line 15—15 in FIG. 13.
Figure 16:
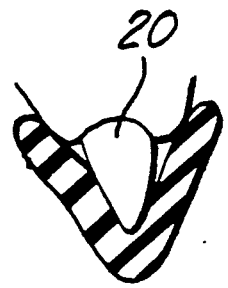
FIG. 16 is a cross sectional view along line 16—16 in FIG. 13.

FIG. 13 depicts another embodiment of a tooth brushing apparatus 100 according to the invention. This embodiment is similar to the embodiment of FIG. 2, but accomplishes tooth cleaning action without bristles. This embodiment comprises a resilient housing 102 containing a channel 104 which fits closely over the arch of teeth, as illustrated in FIGS. 14-16 in the area of a molar 12, canine tooth 16, and front incisor 20, respectively. The cross sectional shape of the channel 104 varies along the arch of teeth according to the shape of each tooth, whereby it snugly fits over all of the teeth to be cleaned. In operation, a user grasps and moves the handles 106 and 108 as in the previously described embodiments. This movement cyclically shifts the position of the housing 102 on the arch of teeth, causing the surface of the channel 104 to rub and clean the teeth and massage the surrounding gums.

The embodiment of FIG. 13 is effective in cleaning the teeth and is cheaper to manufacture than an apparatus having bristles. It is also effective in massaging the gingiva. Nevertheless, the preferred embodiment of the invention includes bristles in order to clean the gingival sulcus effectively.

It will be appreciated that other embodiments of the present invention are possible, such as using a single handle to one side or at the front of the apparatus instead of two handles, using different types of bristles, and varying the shape of the channel, which would vary the angle at which the bristles meet the gingival sulcus. If it is desired, as in the preferred embodiment, to maintain the angle of the bristles to the gingival sulcus at 45 degrees, varying the shape of the channel would also necessitate varying the angle at which the bristles are mounted to the housing. The length of the bristles would also be effected by variations in housing design.

Although the invention has been described with reference to human teeth, it is possible, if modified appropriately, to use it with animals as well.

The preceding description and accompanying drawings are not intended to limit the invention to the specific embodiments described herein, but rather to illustrate a few ways in which the invention may be put into practice. Other embodiments of the invention will be apparent to those skilled in the art. My invention is defined by the following claims:

I claim:

1. An apparatus for brushing teeth, comprising: a resilient arcuate housing, defined by a first arm, a central portion, and a second arm;
    a channel disposed along the length of said housing for placement over an arch of teeth;
    a first handle extending from said first arm of the housing; and
    a second handle extending from said second arm of the housing, whereby movement of said first and second handles back and forth in opposition to each other causes the position of said housing to be cyclically shifted on said arch.

2. The apparatus of claim 1, wherein said first and second handles are rigid and said housing is resilient, whereby said first and second handles and said housing are composed of different materials and said first and second handles are attached to said housing.

3. The apparatus of claim 1, wherein said first and second handles and said housing are composed of the same material and are integral with one another.

4. The apparatus of claim 1, further comprising a plurality of bristles substantially covering the surface of said channel, wherein each bristle is approximately the length of a bristle of a conventional toothbrush.

5. An apparatus for brushing teeth, comprising:
    an arcuate resilient housing defined by a first arm, a central portion, and a second arm;
    a channel adapted for placement over an arch of teeth disposed along the length of said housing, said channel being defined by a first wall, a base portion, and a second wall, said base portion becoming increasingly narrow from the back of said arch to the front of said arch;
    a plurality of bristles disposed generally normal to the surface of said channel, whereby when said channel is placed over said arch, a substantial number of the bristles on the walls of said channel are angled approximately 45 degrees from vertical and said bristles at the base portion of said channel are approximately vertical;
    a first handle disposed on said first arm of said housing; and
    a second handle disposed on said second arm of said housing, whereby movement of said first and second handles back and forth in opposition to each other causes the position of said housing to be cyclically shifted on said arch.

6. An apparatus for brushing both arches of teeth in the mouth at one time, comprising:
    a U-shaped resilient housing, defined by a first arm, a central portion, and a second arm, said housing approximating the shape of the arches of teeth to be brushed;
    a first channel formed in a first side of said housing for placement over a first arch of teeth, said first channel being defined by a first wall, a base portion, and a second wall, said base portion becoming increasingly narrow from the back of said first arch to the front of said first arch;
    a second channel formed in a second side of said housing, opposite said first side, for placement over a second arch of teeth, said second channel being defined by a first wall, a base portion, and a second wall, said base portion becoming increasingly narrow from the back of said second arch to the front of said second arch;
    a plurality of bristles, each approximately the length of a bristle in a conventional toothbrush, substantially covering the surface of each of said first and said second arm of said housing;
    a first handle extending from said first arm of the housing; and
    a second handle extending from said second arm of the housing, whereby movement of said first and second handles back and forth in opposition to each other causes the position of said housing to be cyclically shifted on said arches.

7. An apparatus for brushing teeth, comprising:
    an arcuate resilient housing defined by a first arm, a central portion and a second arm;
    a channel adapted for placement over an arch of teeth disposed along the length of said housing, said channel being defined by a first wall, a base portion, and a second wall, said base portion becoming increasingly narrow from the back of said arch to the front of said arch;
    a plurality of bristles disposed generally normal to the surface of said channel, each of said bristles being approximately the same length as a bristle on a conventional toothbrush, whereby when said channel is placed over said arch, a substantial number of the bristles on the walls of said channel are angled approximately 45 degrees from vertical and said bristles at the base portion of said channel are approximately vertical;
    a first handle extending from said first arm of the housing; and
    a second handle extending from said second arm of the housing, whereby movement of said first and second handles back and forth in opposition to one another causes the position of said housing to be cyclically shifted on said arch and causes the tips of said bristles to move in a circular fashion.

* * * * *